United States Patent
Caruana et al.

(10) Patent No.: US 10,131,638 B1
(45) Date of Patent: Nov. 20, 2018

(54) SYNTHESIS OF AZO INTERMEDIATE

(71) Applicant: The United States of America as Represented by the Secretary of the Navy, Washington, DC (US)

(72) Inventors: Patrick A. Caruana, LaPlata, MD (US); Alfred G. Stern, Upper Marlboro, MD (US); Alex J. Zaita, Houston, TX (US); Thao Vo, Portland, OR (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 15/932,514

(22) Filed: Mar. 12, 2018

(51) Int. Cl.
   *C07D 239/42* (2006.01)
(52) U.S. Cl.
   CPC .................. *C07D 239/42* (2013.01)
(58) Field of Classification Search
   CPC .................................................... C07D 239/42
   USPC ........................................................ 534/578
   See application file for complete search history.

(56) References Cited

U.S. PATENT DOCUMENTS

| 3,120,507 A | 2/1964 | Andrew et al. |
| 6,864,301 B2 | 3/2005 | Ebenezer et al. |
| 8,013,045 B2 | 9/2011 | Ruch et al. |
| 8,273,877 B1 | 9/2012 | Stern et al. |
| 2009/0133787 A1 | 5/2009 | Bley et al. |

OTHER PUBLICATIONS

E. Klingsberg, Pyridine and Its Derivatives, Edition 99, Publisher:John Wiley & Sons, 2009, see Part III, see p. 15 ISBN: 0470188170.
Alan R. Katritzky, Christopher A. Ramsden, John A. Joule, Viktor V. Zhdankin, Handbook of Heterocyclic, Third Edition, Publisher: Elsevier, Oct. 12, 2010; see p. 219, ISBN: 0080958435.
http://www.sciencedirect.com/science/article/pil/S15667367173023; Low temperature liquid phase catalytic oxidation of aniline; promoted by niobium pentoxide micro and nanoparticles; Author links: Wellington M. Ventura", Daniel C. Batalha", Humberto V. Fajardo", Jason G. Taylor", Natalia H. Marins", Bruno S. Noremberg", Tomasz Tanski", Neftali L.V. Carreno", 2017.

*Primary Examiner* — Kristin A. Vajda
(74) *Attorney, Agent, or Firm* — Fredric Zimmerman

(57) ABSTRACT

A synthesis for an azo intermediate, 5,5'-azobis(4-chloropyrimidine) is disclosed. 5,5'-azobis(4-chloropyrimidine) is a relatively stable azo compound in that decomposition does not occur until about 194° C. 5,5'-azobis(4-chloropyrimidine) is a product of oxidative dimerization of 5-amino-4-pyrimidine, which a water soluble compound. The azo intermediate is formed in an aqueous solution, but the azo intermediate is substantially insoluble in water; and as it forms it separates producing a reaction mixture that is a slurry. The azo intermediate is isolated by filtration. The azo intermediate is marginally soluble in acetone. The yield is at least 18%, and the oxidizing agent (bleach) is inexpensive, reaction conditions do not require extreme heat or cold, which taken together make the azo intermediate suitable for scaling up.

21 Claims, 2 Drawing Sheets dissolving a quantity of 5-aminopyrimidine to a volume of water therein forming an aqueous solution of 5-aminopyrimidine;

↓ cooling the aqueous solution of 5-aminopyrimidine to about -5 to 0 °C;

↓ adding dropwise an oxidizing solution of bleach to the aqueous solution of 5-aminopyrimidine over about 2 hours, while maintaining the temperature below 1 °C, therein forming a reaction mixture that is a slurry;

↓ warming the reaction mixture to about 8-10 °C;

↓ filtering the slurry and collecting a filtrate;

↓ washing the filtrate several times with cold water;

↓ drying the filtrate at about room temperature forming a solid, wherein the solid is the azo intermediate.

*Fig. 2*

SYNTHESIS OF AZO INTERMEDIATE

STATEMENT OF GOVERNMENT INTEREST

The invention described herein may be manufactured and used by or for the Government of the United States of America for Governmental purposes without the payment of any royalties thereon or therefore.

BACKGROUND OF THE INVENTION

1. Field of the Invention

The invention relates generally to pyrimidines and more particularly to the synthesis of an azo pyrimidine, which is an intermediate material that is a candidate as a precursor to an energetic material.

2. Background

Oxidative dimerization has been reported in the literature for a number of different products including various manufacturing processes, military applications, and potential pharmaceutical uses.

Synthetic methods for heterocyclic compounds used in dyes and pigments are taught by Adam et al. in US patent publication 2006/0124014 (Adam' 014). The oxidative dimerization reactions described in Adam' 014 require a polar organic solvent, such as dimethyl foramide, which is resistant to oxidation and reactive condensation. A universal problem with this type of solvent is that it is still flammable, and the reaction product is not readily removed. Adam' 014 teaches in [074] that the solvent must be poured on water five times to flush out the dimerized reaction product from the polar organic solvent, before filtering.

Oxidative dimerization of aromatic amines, such as aniline has been reported in J. Org. Chem., 2013, 78 (23), pp 12090-12105. Researchers Okumura et al. found that tert-butyl hypoiodite (tBuOI) oxidatively dimerized aromatic amines to aromatic azo compounds. The researchers mainly focused on coupling different aromatic compounds through an azo linkage, therein forming azo compounds having unsymmetric dimers.

Oxidative dimerization is a broad popular term to describe reactions wherein identical molecules and/or very similar molecules are coupled, typically via dehydrogenation.

SUMMARY OF THE INVENTION

The disclosed invention is an azo intermediate derived from aminopyrimidine and its substituted derivatives such as 5-amino-4-chloropyrimidines.

An object of the invention is that the formed azo intermediate is an oxidative dimer.

A second object of the invention is that the synthesis be conducted in water, which provides an environment that is not flammable, and therefore highly suited to scale up.

A third object of the invention is that the reaction can be conducted at or below room temperature.

A fourth object of the invention is that the yield is 18% or higher.

A fifth object of the invention is that the formed azo intermediate is substantially insoluble in water, and as it forms it precipitates producing a slurry, making the azo intermediate relatively easy to isolate.

A final object of the invention is that the azo intermediate is relatively stable.

BRIEF DESCRIPTION OF THE DRAWINGS

The foregoing invention will become readily apparent by referring to the following detailed description and the appended drawings in which:

FIG. 2 contains a flow diagram of the process steps for synthesizing the azo intermediate.

DETAILED DESCRIPTION OF THE INVENTION

Figure 1:
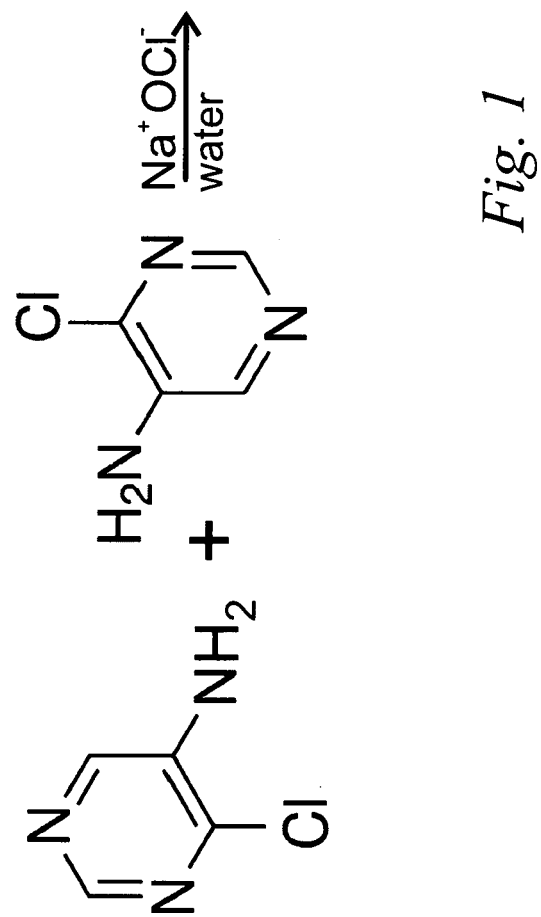
FIG. 1 illustrates the oxidation dimerization of 5-aminopyrimidine, and more specifically 5-amino-4-chloropyrimidine to form an azo intermediate, which generally is 5,5'-azobis(pyrimidine), and more specifically is 5,5'-azobis(4-chloropyrimidine), wherein the oxidizing agent is a hypochlorite, and more specifically sodium hypochlorite dissolved in water.

The invented azo intermediate is a relatively stable azo compound derived from the oxidative dimerization of a 5-aminopyrimidine to form the 5,5'-azobis(pyrimidine). The reader is reminded that 5-aminopyrimidine is a heterocyclic hexagonal aromatic compound wherein the first atom and third atoms are nitrogen. The fifth atom is carbon and it has a pendant nitrogen atom with two hydrogen atoms (e.g.; the amino group (—NH2)).

In the case of the azo compound, during the course of the oxidative dimerization, the hydrogen atoms on two pendant nitrogen atoms (total of four hydrogen atoms) have been removed, and the two pendant nitrogen atoms are coupled by a double bond.

Pyrimidine is soluble in water, alcohol and ether (The Merck Index: 12th edition 1996, New York: Merck. ISBN. 0911910-12-3). 5-aminopyrimidine (CAS No. 591-55-9), which is also known as pyrimidin-5-ylamine, is also soluble in water, as is a halogenated derivative, 5-amino-4-halogen-pyrimidine, and more specifically the chlorine derivative, 5-amino-4-chloropyrimidine (CAS No. 54660-78-5). 5-amino-4-chloropyrimidine has a decomposition temperature of 155-160° C.

Oxidative dimerization, conducted in water, of an 5-aminopyrimidine, and more specifically 5-amino-4-chloropyrimidine, produces an azo dimer, 5,5'-azobis(4-chloropyrimidine), that is substantially insoluble in water. As oxidative dimerization occurs, the formed azo dimer separates from the water.

The process for synthesizing and isolating the azo dimer is illustrated in FIG. 2. The process includes the steps of: dissolving a quantity of an aminopyrimidine in a volume of room temperature water therein forming an aqueous solution of aminopyrimidine; cooling the aqueous solution of aminopyrimidine to about −5 to 0° C.; adding dropwise an oxidizing solution of a bleach to the aqueous solution of aminopyrimidine over about 2 hours, while maintaining the temperature below 1° C., therein producing a reaction mixture which is a slurry; warming the reaction mixture to about 8-10° C.; filtering the slurry, and collecting the filtrate. The filtrate is washed several times with cold water, and then dried at about room temperature forming a solid. In the case where the solid is 5,5'-azobis(4-chloropyrimidine), the solid is salmon colored. The azo dimer of aminopyrimidine is stable, and is suitable as an azo intermediate that can used as a precursor to an energetic material.

Drying is nominally assisted by a vacuum. Depending on the specific azo dimer, the solid can vary in color. The yield of the azo dimer is at least 18%.

Typically the bleach is about 10%-13% sodium hypochlorite in water. The stoichiometric quantity is at least one mole of bleach per mole of aminopyrimidine, and more specifically per mole of 5-amino-4-chloropyrimidine. To drive the reaction to completion, a molar excess of bleach is preferably used. As is described below the molar excess ratio of bleach to 5-amino-4-chloropyrimidine is often 6:1 or higher.

While washing purifies the azo dimer, purity can be enhanced by triturating it with acetone at room temperature. The azo dimer is only minimally soluble in acetone, while most impurities have good solubility in acetone. It is anticipated that other solvents may also be suitable for trituration.

The process for synthesizing and characterizing a specific azo intermediate, 5,5'-azobis(4-chloropyrimidine) is show in FIG. 1 and described below.

5-amino-4-chloropyrimidine (4.00 g, 30.9 mmol.) is dissolved in room temperature water (200 mL), and then cooled to about −5 to 0° C. in a salt/ice bath. An oxidizing solution (bleach about 10%-136 sodium hypochlorite, ~126 mL, ~204 mmol. (a stoichiometric molar ratio of sodium hypochlorite:5-amino-4-chloropyrimidine of about 6.6:1)) is then added dropwise, over about 2 hours, while maintaining the temperature below 1° C., therein forming a reaction mixture which is a dilute slurry. The reaction mixture is then warmed to about 8-10° C. for about 30 minutes, completing oxidative dimerization of the 5-amino-4-chloropyrimidine, which is then filtered. The filtrate is washed with cold water three times, and dried under vacuum at about room temperature to afford the azo dimer (0.89 g, ~23% yield) as a salmon colored solid, which is confirmed to be 5,5'-azobis (4-chloropyrimidine).

The azo dimer may be further purified by triturating with acetone (0.076 g/mL) at room temperature. Trituration improves the purification of an impure compound by taking advantage of the solubility differences of the compound versus its impurities in a solvent (or solvent mixture). 5,5'-azobis(4-chloropyrimidine) is only slightly soluble in acetone, but impurities, such as 5-amino-4-chloropyrimidine and water, are very soluble in acetone.

The formed azo dimer was characterized as having a melting point of about 194° C. (with broad decomposition). Proton NMR (@300 MHz using hexadeuteroacetone as a solvent): δ 9.18 (s, 2H), 8.96 (s, 2H); IR: 3033, 1539, 1421, 1389, 1278, 1219, 1131, 1110 cm−1; GC-MS: calculated for C8H4Cl2N6 [M]+, 253.9874; found, 254.0. MS-DART ionization-positive (m/z): calculated for C8H5Cl2N6 [M+H]+, 254.9953; found, 254.9965. Analysis calculated weight percent for C8H4Cl2N6: C, ~37.67; H, ~1.58; N, ~32.95; found weight percent is C, ~37.72; H, ~1.58; N, ~33.01.

The reader is reminded that chlorine atoms have a weighted average atomic mass of ~35.5, but only 35 for the predominate isotope. The GC-MS dominant peak reflects this, and the MS-DART analysis reflects the actual atomic weight plus a proton. The analysis calculated weight percent reflects weighted average atomic weight of ~35.5.

The synthesis of the azo intermediate is shown in FIG. 1. Two molecules of 5-amino-4-chloropyrimidine have been oxidatively dimerized into 5,5'-azobis(4-chloropyrimidine). The two amino nitrogen atoms have lost their hydrogens, and are joined with a double bond, therein forming the azo dimer. The oxidative dimerization is facilitated by the oxidizing agent, chlorine in a caustic soda aqueous solution (i.e. sodium hypochlorite).

A probable reaction mechanism is chlorination of 5-amino-4-chloropyrimidine to a 5-chloramine-4-chloropyrimidine intermediate. A second molecule of 5-amino-4-chloropyrimidine displaces chlorine to make a hydrazo intermediate. There is further chlorination of the hydrazo intermediate, and then elimination of chloride creating the azo dimer, 5,5'-azobis(4-chloropyrimidine).

The azo intermediate is very stable in that it has a melting point of about 194° C. (with broad decomposition).

The other objects of the invention have also clearly have been met or exceeded. A significant advantage of the invented synthesis of the azo intermediate is that there is spontaneous phase separation, as evidenced by the formation of the slurry. When the azo intermediate, is formed, it precipitates from the aqueous solution as a solid, which is nominally colored. The solid precipitate can easily be separated using filtration from the aqueous solution, wherein the filtrate is a relatively pure compound.

Finally, any numerical parameters set forth in the specification and attached claims are approximations (for example, by using the term "about") that may vary depending upon the desired properties sought to be obtained by the present invention. At the very least, and not as an attempt to limit the application of the doctrine of equivalents to the scope of the claims, each numerical parameter should at least be construed in light of the number of significant digits and by applying ordinary rounding.

What is claimed is:

1. A process for synthesizing an azo intermediate, said process comprising the steps of:
    dissolving a quantity of 5-aminopyrimidine in a volume of water therein forming an aqueous solution of 5-aminopyrimidine;
    cooling the aqueous solution of 5-aminopyrimidine to about −5 to 0° C.;
    adding dropwise an oxidizing solution of bleach to the aqueous solution of 5-aminopyrimidine over about 2 hours, while maintaining the temperature below 1° C., therein forming a reaction mixture that is a slurry;
    warming the reaction mixture to about 8-10° C.;
    filtering the slurry, therein collecting a filtrate;
    washing the filtrate several times with cold water; and
    drying the filtrate at about room temperature, wherein the dry filtrate is the azo intermediate.

2. The process according to claim 1, wherein drying is assisted by utilizing a vacuum.

3. The process according to claim 1, wherein the solid is colored.

4. The process according to claim 1, wherein the aqueous solution of 5-aminopyrimidine is formed at room temperature.

5. The process according to claim 1, wherein the yield of the azo intermediate is at least 18%.

6. The process according to claim 1, wherein the bleach is about 10%-13% sodium hypochlorite in water.

7. The process according to claim 1, wherein the azo intermediate may be further purified by triturating it with acetone at room temperature.

8. The process according to claim 1, wherein the stoichiometric quantity is at least one mole of bleach per mole of the 5-aminopyrimidine.

9. A process for synthesizing an azo intermediate, comprising:
    dissolving a quantity of 5-amino-4-chloropyrimidine in a volume of water therein forming an aqueous solution of 5-amino-4-chloropyrimidine;

cooling the aqueous solution of 5-amino-4-chloropyrimidine to about −5 to 0° C.;

adding dropwise an oxidizing solution of bleach to the aqueous solution of 5-amino-4-chloropyrimidine over about 2 hours, while maintaining the temperature below 1° C., therein forming a reaction mixture that is a slightly salmon colored slurry;

warming the reaction mixture to about 8-10° C. therein completing oxidative dimerization of the 5-amino-4-chloropyrimidine;

filtering the slurry collecting a filtrate;

washing the filtrate several times with cold water; and drying the filtrate at about room temperature forming a solid, wherein the solid is the azo intermediate comprised of 5,5'-azobis(4-chloropyrimidine).

10. The process according to claim 9, wherein drying is assisted by utilizing a vacuum.

11. The process according to claim 9, wherein the solid is salmon colored.

12. The process according to claim 9, wherein the aqueous solution of 5-amino-4-chloropyrimidine is formed at room temperature.

13. The process according to claim 9, wherein the yield of the azo intermediate comprised of 5,5'-azobis(4-chloropyrimidine) is at least 18%.

14. The process according to claim 9, wherein the bleach is about 10%-13% sodium hypochlorite in water.

15. The process according to claim 9, wherein the azo intermediate may be further purified by triturating it with acetone at room temperature.

16. The process according to claim 9, wherein the stoichiometric quantity is at least one mole of bleach per mole of the 5-amino-4-chloropyrimidine.

17. An azo intermediate comprised of 5,5'-azobis(4-chloropyrimidine), wherein said 5,5'-azobis(4-chloropyrimidine) has a structure as shown below:

18. The azo intermediate according to claim 17, wherein said azo intermediate has a melting point of about 194° C. (with broad decomposition).

19. The azo intermediate according to claim 17, wherein said azo intermediate has a Proton NMR (@300 MHz using hexadeuteroacetone as a solvent), four hydrogen atoms, two hydrogen atoms with a NMR shift at 9.18 and another two hydrogen atoms at 8.96.

20. The azo intermediate according to claim 17, wherein said azo intermediate has an Infrared wavelength absorption spectrum at about: 3033, 1539, 1421, 1389, 1278, 1219, 1131, 1110 cm−1.

21. The azo intermediate according to claim 17, wherein said azo intermediate has a GC-MS actual weight: calculated for C8H4Cl2N6 [M]+, 253.9874; C8H4Cl2N6 found, 254.0; an MS-DART ionization-positive (m/z): calculated for C8H5Cl2N6 [M+H]+, 254.9953; found weight, 254.9965; and an analytical calculated weight percent for C8H4Cl2N6: C, ~37.67%; H, ~1.58%; N, ~32.95%; and a found weight percent: C, ~37.72%; H, ~1.58%; N, ~33.01%.

* * * * *